United States Patent [19]

Hambleton

[11] Patent Number: 4,699,765
[45] Date of Patent: Oct. 13, 1987

[54] DEVICE FOR DETECTING THE PRESENCE OF AIR IN A STEAM STERILISER

[75] Inventor: Roger Hambleton, Stockport, England

[73] Assignee: The Victoria University of Manchester, Manchester, England

[21] Appl. No.: 629,904

[22] Filed: Jul. 11, 1984

[30] Foreign Application Priority Data

Jul. 15, 1983 [GB] United Kingdom ............... 8319205

[51] Int. Cl.⁴ .................... G01N 31/22; G01N 37/00
[52] U.S. Cl. ...................................... 422/57; 422/58; 422/61; 436/1
[58] Field of Search ................ 436/1; 422/55, 56, 57, 422/61, 86, 87, 88, 158; 435/31; 206/438, 439

[56] References Cited

U.S. PATENT DOCUMENTS

| | | | |
|---|---|---|---|
| 2,249,867 | 1/1938 | Snelling | 422/56 |
| 3,523,011 | 8/1970 | Bhiwandker et al. | 422/57 |
| 3,745,057 | 7/1973 | Loft et al. | 206/439 |
| 3,930,580 | 1/1976 | Bazell et al. | 206/439 |
| 3,938,658 | 2/1976 | Rohde | 206/439 |
| 4,087,332 | 5/1978 | Hansen | 422/56 |
| 4,195,056 | 3/1980 | Patel | 422/56 |
| 4,382,063 | 5/1983 | Romito et al. | 422/57 |
| 4,410,493 | 10/1983 | Joslyn | 422/56 |
| 4,478,792 | 10/1984 | McConnaughey et al. | 422/56 |
| 4,486,387 | 12/1984 | Augurt | 422/58 |

OTHER PUBLICATIONS

Bowie et al.; *The Lancet;* Mar. 16, 1963; pp. 586-587.

*Primary Examiner*—Barry S. Richman
*Assistant Examiner*—C. M. Delahunty
*Attorney, Agent, or Firm*—Nies, Webner, Kurz & Bergert

[57] ABSTRACT

A device for testing the efficiency of autoclaves of the type used in hospitals for steam sterilizing porous loads such as surgical dressings, and particularly for detecting the presence of air in such a system, comprising first and second porous masses (10, 11) of a substantially manmade material such as spun bonded polypropylene, superimposed so as to sandwich therebetween an indicator sheet (12) and a pair of porous and absorbent sheets (12a). This assembly is held firmly together within a perforated stainless steel box (13) having a closable lid (14). For the test the whole device is placed in a steam sterilizer under normal working conditions. Subsequently, the test device is removed and the indicator sheet (12) inspected, any color variation across the sheet providing an indication of incomplete sterilizing conditions.

15 Claims, 2 Drawing Figures

DEVICE FOR DETECTING THE PRESENCE OF AIR IN A STEAM STERILISER

This invention concerns a device for testing the efficiency of autoclaves of the type used in hospitals for sterilising porous loads such as surgical dressings, and particularly for detecting the presence of air in such a system.

Porous loads are sterilised by subjecting them to saturated steam at a temperature of between 134° C. and 138° C. for a period of not less than 3 minutes. In order to ensure correct sterilising conditions, the steam must penetrate unhindered to the centre of the load. This can be achieved only if all of the air is first removed from the steriliser vessel and its load and this is accomplished typically by a process of evacuation and steam flushing of the sterilising vessel and its load.

Failure to remove all of the air or the subsequent leakage of air into an evacuated chamber, or the introduction of air in the steam supply, causes air pockets to remain within the porous load, usually in the inner regions thereof. In this case the temperature within the load might be lower in some places than that required during all or part of the sterilisation process.

The standard test for the efficiency of air removal in autoclaves is known as the Bowie/Dick towel test. This test utilises a stack of standard linen Huckaback towel measuring some 270 mm high and about 300 mm×200 mm in plan. At about the vertical centre of the stack there is placed a sheet of paper bearing so-called autoclave tape or other indicator which undergoes a change in appearance in the presence of certain levels of moisture and temperature. The test pack is processed in the autoclave and the satisfactory result would show and even change in appearance across the whole of the indicator sheet, whereas the presence of air in the stack is indicated by a failure of the indicator to change its appearance in certain areas, usually at the centre. This test must be carried out daily before the autoclave is used for the production of sterile porous loads.

There are certain disadvantages associated with this known test. For example, the standard towel stack is too large to fit into many small-chambered autoclaves. Furthermore the Huckaback towels are expensive and usually require to be laundered at least once a week. The towels require to be aired carefully between tests, and they deteriorate gradually and become unusable within about 12 months of normal use. This is because the fibrous consistency becomes matted so that steam cannot readily diffuse through it, thus increasing the risk of misleading test results. Furthermore, Huckaback towels, being made from natural fibre, can give rise to exothermic reactions, i.e. they will absorb moisture very readily with the release of heat, when they are too dry. In the case of the Bowie/Dick test such a phenomenon can result in the temperature within the pack being higher than the temperature in the autoclave chamber and again this can lead to misleading test results.

An object of the present invention is to provide a device in the form of a test kit for detecting the presence of air in a steam steriliser, wherein most of the disadvantages just referred to, are overcome.

Thus according to the present invention there is provided a test device for detecting the presence of air in a steam steriliser, comprising a first porous mass of at least substantially man-made material, a second porous mass of a similar material, an indicator adapted to undergo a visual change under moist heat sterilising conditions and sandwiched between the masses thus to be in intimate contact therewith, and means for removably holding the masses and indicator in close superimposed relationship, said means being permeable to allow the free passage of air and steam to the external surfaces of said masses.

The term substantially man-made material shall be construed as to include all materials which are or may be formed into a porous mass and constituted principally by synthetic fibres.

An embodiment of the invention will now be described, by way of example only, with reference to the accompanying schematic drawings in which.

Figure 1:
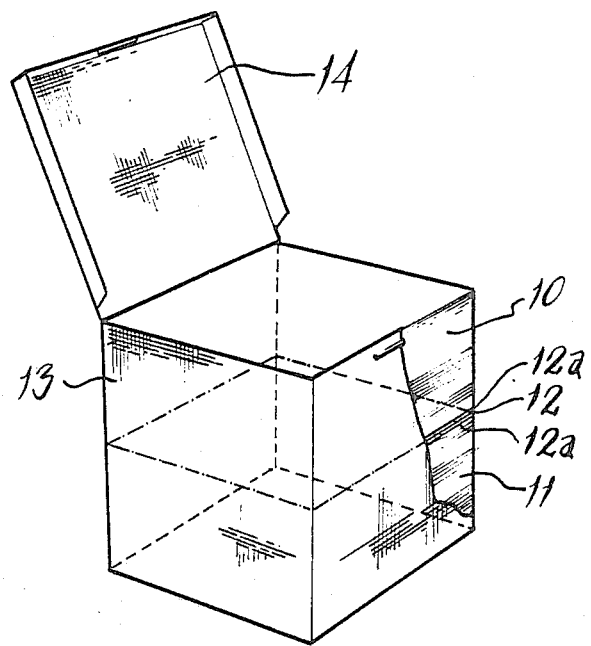
FIG. 1 is a perspective view of the device.
Figure 2:
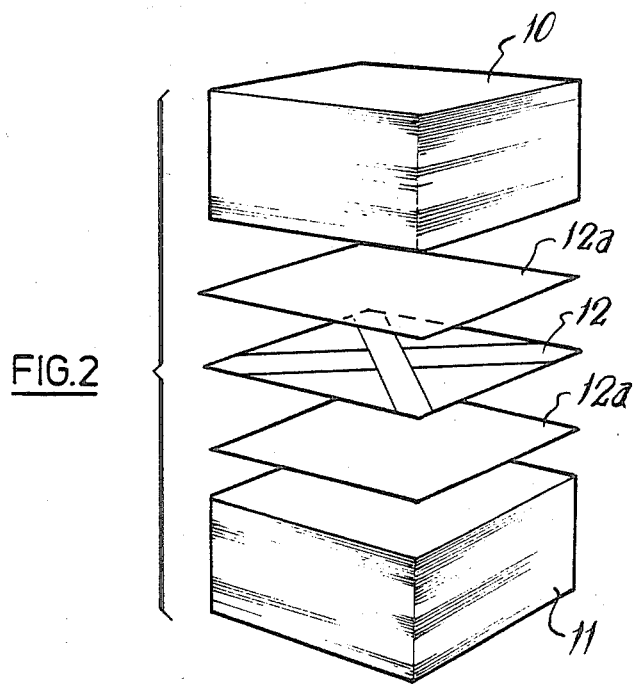
FIG. 2 is an exploded view of some of the constituent parts thereof.

Referring now to the drawings, a device made in accordance with the invention comprises first and second porous masses 10 and 11 each formed from a stack of single sheets of a man-made fibre woven or non-woven material such as spun bonded polypropylene having a weight in the region of 50–100 grammes per square metre. Each mass contains an appropriate number (typically about 130) of such sheets arranged in close superimposed relationship. Sandwiched between the masses 10 and 11 is a sheet of paper 12 bearing an indicator, for example in the form of strips of so-called autoclave tape conveniently in the shape of a St. Andrews cross. The indicator is adapted to undergo a visual change under moist heat sterilising conditions.

A further sheet 12a of a porous and absorbent material such as paper is interposed between each face of sheet 12 and the adjacent surface of the mass 10 or 11. This may take the form of unglazed paper (bond) of weight typically 80 g per square metre.

The masses 10 and 11, sheets 12a and indicator 12 are placed in close superimposed relationship into a box 13 as a close fit therewithin. The box has a lid 14 which when closed applies a slight compressive force to its contents to ensure that they are firmly held together. The box 13 may be of stainless steel or plastics and has perforated walls to allow free access of air and steam to the contents.

As can be seen from the drawing, the pack when assembled is approximately cuboid and it has a side dimension typically in the region of 12–15 cm.

The man-made fibre from which the masses 10 and 11 are produced shall not give rise to exothermic reactions when hydrated and must exhibit air/steam penetration characteristics similar to those of Huckaback towels which comply with British Standard BS 1781 (TL6/TL/5).

Experimental work has demonstrated that the device as described is capable of detecting the presence of air in an autoclave. It is also clear from temperature measurements made within the device that the presence of air leads to a depression of temperature at the centre of the test pack similar to that observed with the Huckaback towel pack used in the conventional Bowie/Dick test.

The presence of the absorbent sheets 12a ensures an even distribution of moisture across the surface of sheet 12 and prevents the formation thereon of droplets of moisture from the non-absorbent but porous man-made material of masses 10 and 11.

The man-made fibre from which the masses 10 and 11 are produced will not adsorb moisture with a consequent release of heat as is common with packs made from natural fibre, so that misleading test results should be avoided. Similarly, the man-made fibre needs little or no preparation for re-use. After use, the pack is removed from the container and simply allowed to dry out at room temperature for about twenty four hours or less. The fibre will not deteriorate rapidly and is expected to have a much greater life span than the conventional Huckaback towel.

Whilst the masses 10 and 11 have been described as constituted by superimposed sheets, it is conceivable that they can be produced as composite blocks of a needled or other non-woven man-made fibre.

If the masses 10 and 11 are produced in sheet form, large sheets are assembled and cut to the required size using a band saw or similar device which tends to heat-seal the cut edges together thus facilitating the subsequent handling of the stacks as formed bundles, in use. Alternatively, to prevent the sheets from separating, they may be attached together by stitching or by wrapping or strapping with a porous material which may be the same as that from which the sheets are made.

It is not intended to limit the invention to the above example only, many variations, such as might readily occur to one skilled in the art, being possible without departing from the scope of the invention as defined by the appended claims.

For example, whilst the box 13 is likely to be the most convenient container for the test stack, the stack can, alternatively, be simply strapped together using a porous tape, or pre-wrapped with an air and steam permeable wrapping during manufacture and opened only after the test has been carried out to reveal the indicator sheet.

Furthermore, instead of autoclave tape applied to a paper sheet, the indicator may be a paper sheet bearing a substance having similar chemical properties.

What is claimed is:

1. A reusable test device for detecting the presence of air in a steam sterilizer, comprising a first porous and non-absorbent mass of at least substantially man-made fibre, a second porous and non-absorbent mass of a similar fibre, said fibre being selected to be that which will not give rise to exothermic reaction when hydrated, said masses being of substantially uniform porosity throughout the respective masses, an indicator adapted to undergo a visual change under moist heat sterilizing conditions and sandwiched between the masses thus to be in intimate contact therewith, and holding means for removably holding the masses and indicator under a compressive force sufficient to maintain said masses and said indicator in close superimposed relationship, said means being positioned directly adjacent said masses and being permeable to allow the free passage of air and steam to the external surfaces of said masses.

2. A test device according to claim 1, wherein each said porous mass is formed from a stack of single sheets of said man-made fibre.

3. A test device according to claim 1, wherein said man-made fibre is non-woven spun bonded polypropylene.

4. A test device according to claim 1, wherein said first and second porous masses and said indicator, when superimposed and contained within said holding means, form a pack which is substantially cuboid and has a side dimension in the region of 12–15 cm.

5. A test device according to claim 1, wherein said indicator comprises a sheet of paper bearing strips of autoclave tape.

6. A test device according to claim 5, including, between each face of said indicator sheet and the adjacent surface of said first or second porous mass, a sheet of a porous and absorbent material.

7. A test device according to claim 6, wherein said sheet of porous and absorbent material is unglazed paper of a weight in the region of 80 g per square metre.

8. A test device according to claim 2, wherein each said porous mass is produced by the sides of said stack having been cut to a required size in such a manner that the cut edges are at least partially heat-sealed whereby the single sheets will not readily part in use.

9. A test device according to claim 2, wherein the sheets of each said stack are attached together.

10. A test device according to claim 1, wherein said holding means comprises a box having a closable lid and perforated walls to permit free access of air and steam to its contents, the box comprising a close fit for said contents such that a slight compressive force is applied thereto when the lid is closed thus to ensure that the contents are firmly held together.

11. A test device according to claim 10, wherein said box is formed from stainless steel.

12. A test device according to claim 10, wherein said box is formed from plastics.

13. A test device according to claim 1, wherein each said porous mass is produced as a composite block of a non-woven, substantially man-made fibre.

14. A test device according to claim 1, wherein said holding means for removably holding the masses and indicator in close superimposed relationship comprises a strapping of porous tape.

15. A test device according to claim 1, wherein said means for removably holding the masses and indicator in close superimposed relationship comprises a permeable wrapping applied during manufacture and positioned and arranged to be opened only after a test has been carried out, in order to reveal the indicator.

* * * * *